United States Patent
Takahashi et al.

(10) Patent No.: US 12,075,969 B2
(45) Date of Patent: Sep. 3, 2024

(54) INFORMATION PROCESSING APPARATUS, CONTROL METHOD, AND NON-TRANSITORY STORAGE MEDIUM

(71) Applicants: NEC CORPORATION, Tokyo (JP); NATIONAL CANCER CENTER, Tokyo (JP)

(72) Inventors: Ikuma Takahashi, Tokyo (JP); Maki Sano, Tokyo (JP); Kimiyasu Takoh, Tokyo (JP); Motoyasu Okutsu, Tokyo (JP); Chiemi Tanaka, Tokyo (JP); Masahiro Saikou, Tokyo (JP); Hitoshi Imaoka, Tokyo (JP); Kenichi Kamijo, Tokyo (JP); Ryuji Hamamoto, Tokyo (JP); Yutaka Saito, Tokyo (JP); Masayoshi Yamada, Tokyo (JP)

(73) Assignees: NEC CORPORATION, Tokyo (JP); NATIONAL CANCER CENTER, Tokyo (JP)

(*) Notice: Subject to any disclaimer, the term of this patent is extended or adjusted under 35 U.S.C. 154(b) by 677 days.

(21) Appl. No.: 17/274,286

(22) PCT Filed: Sep. 12, 2019

(86) PCT No.: PCT/JP2019/035926
§ 371 (c)(1),
(2) Date: Mar. 8, 2021

(87) PCT Pub. No.: WO2020/071086
PCT Pub. Date: Apr. 9, 2020

(65) Prior Publication Data
US 2022/0110505 A1   Apr. 14, 2022

(30) Foreign Application Priority Data
Oct. 4, 2018  (JP) .................................. 2018-189241

(51) Int. Cl.
*A61B 1/00*   (2006.01)
*G06T 7/00*   (2017.01)

(52) U.S. Cl.
CPC .... *A61B 1/00006* (2013.01); *A61B 1/000094* (2022.02); *A61B 1/00045* (2013.01);
(Continued)

(58) Field of Classification Search
CPC .......... A61B 1/00006; A61B 1/000094; A61B 1/00045; A61B 1/00055; G06T 7/0012;
(Continued)

(56) References Cited

U.S. PATENT DOCUMENTS 8,861,783 B1    10/2014 Peleg
9,430,706 B1 *   8/2016 Peleg ..................... G06V 20/49
(Continued)

FOREIGN PATENT DOCUMENTS

EP        3 360 461 A1      8/2018
JP        2012-249936 A    12/2012
(Continued)

OTHER PUBLICATIONS

International Search Report of PCT/JP2019/035926 dated Nov. 26, 2019 [PCT/ISA/210].
(Continued)

*Primary Examiner* — Dhaval V Patel
(74) *Attorney, Agent, or Firm* — Sughrue Mion, PLLC

(57) ABSTRACT

An information processing apparatus (2000) detects an abnormal region (30) in each of a plurality of video frames (14) constituting video data (12) in which the inside of a body is captured. The information processing apparatus (2000) outputs output information related to the detected abnormal region (30). Herein, the information processing apparatus (2000) starts outputting of the output information when a detection score based on a proportion of the number
(Continued)

of the video frames (14) in which the abnormal region (30) is detected becomes equal to or more than a first threshold value in a state where outputting of the output information is not being performed. Further, the information processing apparatus (2000) ends outputting of the output information when the detection score becomes equal to or less than a second threshold value in a state where outputting of the output information is being performed.

13 Claims, 8 Drawing Sheets

(52) U.S. Cl.
CPC .. *G06T 7/0012* (2013.01); *G06T 2207/10016* (2013.01); *G06T 2207/10068* (2013.01); *G06T 2207/30204* (2013.01)

(58) Field of Classification Search
CPC . G06T 2207/10016; G06T 2207/10068; G06T 2207/30204; G06T 2207/10024; G06T 2207/20076; G06T 2207/20081; G06T 2207/20084; G06T 2207/30028; G06T 2207/30096
See application file for complete search history.

(56) References Cited

U.S. PATENT DOCUMENTS

| | | | |
|---|---|---|---|
| 10,685,432 B2 * | 6/2020 | Kasahara | G06T 7/0002 |
| 10,757,125 B2 * | 8/2020 | Wakasugi | G06N 3/08 |
| 11,100,633 B2 * | 8/2021 | Ngo Dinh | G06T 7/0012 |
| 11,103,197 B2 | 8/2021 | Kamon | |
| 11,170,498 B2 * | 11/2021 | Kono | A61B 1/018 |
| 11,609,689 B2 * | 3/2023 | Rabinovitz | G11B 27/005 |
| 2017/0098301 A1 | 4/2017 | Ikemoto et al. | |
| 2018/0249900 A1 | 9/2018 | Imaizumi et al. | |
| 2019/0069757 A1 | 3/2019 | Iwaki et al. | |

FOREIGN PATENT DOCUMENTS

| | | |
|---|---|---|
| JP | 2015-112429 A | 6/2015 |
| JP | 2016-158681 A | 9/2016 |
| JP | 2017-060806 A | 3/2017 |
| WO | 2017/081976 A1 | 5/2017 |
| WO | 2017/203560 A1 | 11/2017 |
| WO | 2018/198161 A1 | 11/2018 |
| WO | 2018/216617 A1 | 11/2018 |
| WO | 2018/216618 A1 | 11/2018 |

OTHER PUBLICATIONS

Extended European Search Report dated Oct. 29, 2021 in European Application No. 19869862.3.
Office Action dated Feb. 14, 2023 from the Japanese Patent Office in Application No. 2020-550252.
Office Action dated Apr. 19, 2022 by the Japanese Patent Office in Japanese Application No. 2020-550252.

* cited by examiner

HATCHING

DOT PATTERN

MARK INDICATING
CENTER POSITION

RECTANGULAR FRAME

BOUNDARY FRAME

ELLIPTIC FRAME

INFORMATION PROCESSING APPARATUS, CONTROL METHOD, AND NON-TRANSITORY STORAGE MEDIUM

CROSS REFERENCE TO RELATED APPLICATIONS

This application is a National Stage of International Application No. PCT/JP2019/035926, filed Sep. 12, 2019, claiming priority to Japanese Patent Application No. 2018-189241, filed Oct. 4, 2018, the contents of all of which are incorporated herein by reference in their entirety.

TECHNICAL FIELD

The present invention relates to an inspection of the inside of a body of a person and another animal by using a captured image.

An inspection of determining whether there is an abnormality inside a body of a person and an animal is performed by using an image in which the inside of the body is captured. One example thereof is endoscopy. In endoscopy, a doctor inserts a scope with a camera provided at a tip from a nose, a mouth, an anus, or the like of a subject, and moves the scope inside a body. In this way, a state inside the body is captured by the camera. A doctor checks whether there is an abnormal portion inside the body of the subject while viewing a video representing, on a display apparatus, the state inside the body being captured by the camera.

A technique for assisting such an inspection using an image has been developed. For example, PTL 1 discloses a technique for being able to easily distinguish a lesion from another portion by detecting the lesion in an image and changing a tone of the detected lesion to a tone different from that of the another portion. PTL 2 discloses a technique for detecting a lesion included in an image, computing seriousness of the lesion, and marking a mark indicating a position and the seriousness of the lesion on the image. PTL 3 discloses a technique for outputting an icon related to a lesion in a display mode according to a size of the lesion when the lesion is detected in an image. PTL 4 discloses a technique for emphasizing and displaying a position associated with a possible lesion region when the possible lesion region is continuously detected in an observation image in a system for displaying an observation image generated by an endoscope apparatus.

RELATED DOCUMENT

Patent Document

[PTL 1] Japanese Patent Application Publication No. 2017-060806
[PTL 2] Japanese Patent Application Publication No. 2016-158681
[PTL 3] Japanese Patent Application Publication No. 2015-112429
[PTL 4] International Publication No. WO2017/081976

SUMMARY OF THE INVENTION

Technical Problem

In a method of performing an inspection by moving a camera inside a body of a subject, the camera is moved inside a body, and thus a portion that can be observed by a doctor changes with time. Thus, there is a possibility that a doctor may miss an abnormal portion, and there is actually a difference in a lesion detection rate among doctors who are in charge of an inspection. Thus, various techniques for assisting an inspection are required in order to improve quality of an inspection using an image in which the inside of a body of a subject is captured.

The present invention has been made in view of the above-described problem. One of objects of the present invention is to provide a new technique for improving quality of an inspection using an image in which the inside of a body of a subject is captured.

Solution to Problem

An information processing apparatus according to the present invention includes 1) a detection unit that detects an abnormal region being an image region inferred to represent an abnormal portion inside a body in each of a plurality of video frames constituting a video in which the inside of the body is captured, and 2) an output unit that outputs output information related to the detected abnormal region.

The output unit starts outputting of the output information when a score based on a proportion of the number of video frames in which the abnormal region is detected becomes equal to or more than a first threshold value in a state where outputting of the output information is not being performed, and ends outputting of the output information when the score becomes equal to or less than a second threshold value in a state where outputting of the output information is being performed. The second threshold value is smaller than the first threshold value.

A control method according to the present invention is executed by a computer. The control method includes 1) a detection step of detecting an abnormal region being an image region inferred to represent an abnormal portion inside a body in each of a plurality of video frames constituting a video in which the inside of the body is captured, and 2) an output step of outputting output information related to the detected abnormal region.

In the output step, outputting of the output information is started when a score based on a proportion of the number of video frames in which the abnormal region is detected becomes equal to or more than a first threshold value in a state where outputting of the output information is not being performed, and outputting of the output information is ended when the score becomes equal to or less than a second threshold value in a state where outputting of the output information is being performed. The second threshold value is smaller than the first threshold value.

A program according to the present invention causes a computer to execute each step included in the control method according to the present invention.

Advantageous Effects of Invention

The present invention provides a new technique for improving quality of an inspection using an image in which the inside of a body of a subject is captured.

BRIEF DESCRIPTION OF THE DRAWINGS

The above-described object, the other objects, features, and advantages will become more apparent from suitable example embodiments described below and the following accompanying drawings.

DESCRIPTION OF EMBODIMENTS

Figure 1:
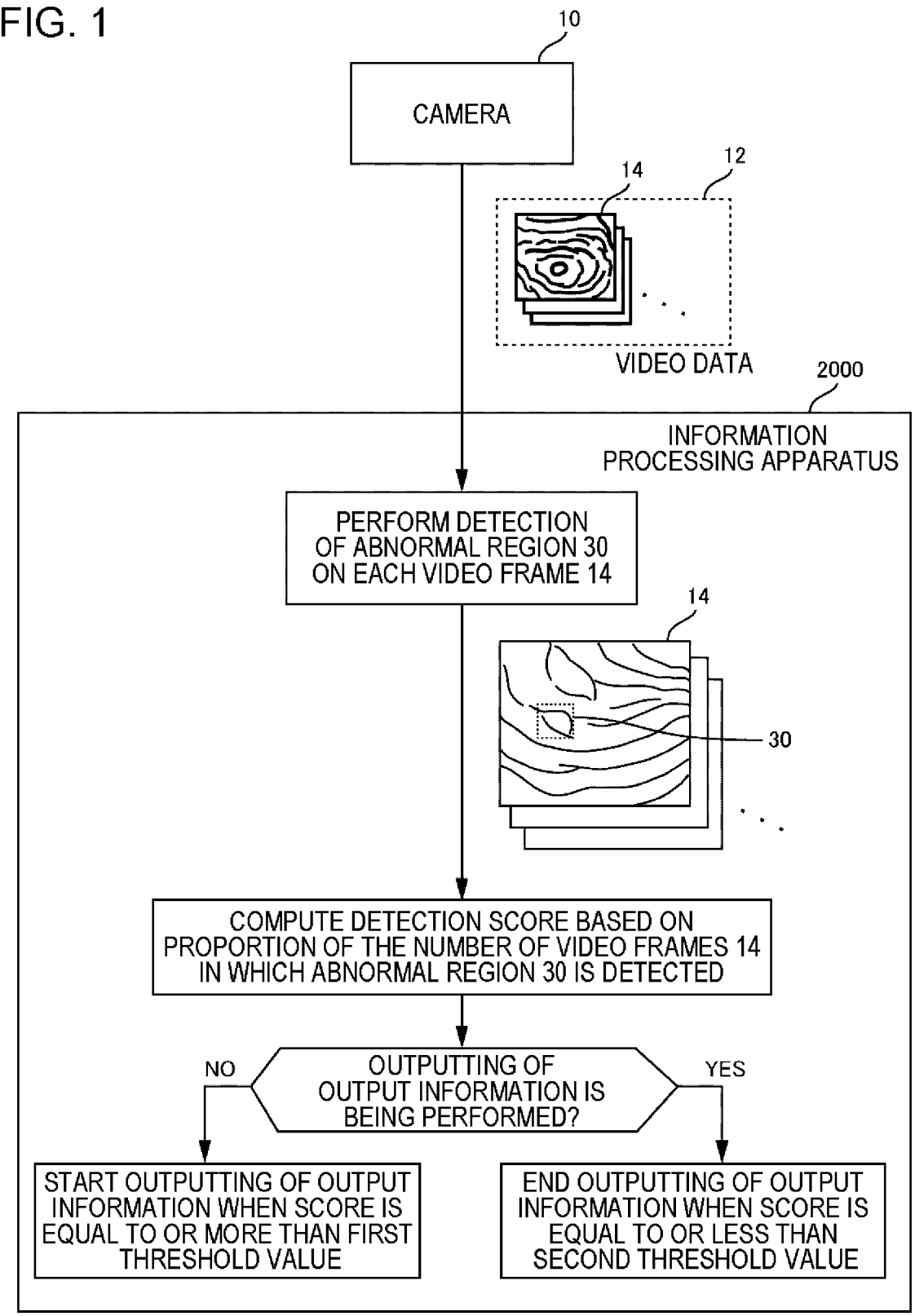
FIG. 1 is a diagram schematically illustrating an information processing apparatus according to an example embodiment 1.

Hereinafter, example embodiments of the present invention will be described with reference to the drawings. It should be noted that, in all of the drawings, similar components have similar reference numerals, and description thereof will be appropriately omitted. Further, in each block diagram, each block represents a configuration of a functional unit instead of a configuration of a hardware unit unless otherwise described.

Example Embodiment 1

FIG. 1 is a diagram schematically illustrating an information processing apparatus 2000 according to an example embodiment 1. FIG. 1 merely illustrates one example of an operation of the information processing apparatus 2000 for facilitating understanding of the information processing apparatus 2000, and does not limit a function of the information processing apparatus 2000 in any way.

A camera 10 is used for an inspection of a person and another animal. Hereinafter, a person to be inspected and the like are referred to as a subject. The camera 10 is any camera capable of capturing the inside of a body of a subject, and generates a video frame 14 representing a capturing result thereof. For example, the camera 10 is an endoscope camera. Video data 12 are constituted by a plurality of video frames 14 generated at times different from each other.

A user (for example, a doctor) of the information processing apparatus 2000 recognizes a state inside a body of a subject by viewing the video data 12. More specifically, the user recognizes whether there is an abnormal portion inside a body of a subject, a degree of the abnormality, and the like. Herein, the "abnormal portion inside a body" is, for example, a portion with a lesion, a wounded portion, a portion with a foreign body, or the like. The lesion is a change in a living body that occurs due to a disease, and is, for example, a tumor and the like.

Herein, an improved accuracy of endoscopy and the like can be expected by providing useful information acquired by analyzing the video data 12. For example, in endoscopy, a doctor and the like search for an abnormal portion inside a body of a subject while observing the inside of the body with a camera. At this time, although an abnormal portion is captured by the camera, there is a possibility that the doctor may miss the abnormal portion. Thus, it is suitable to assist in such a way that the doctor easily recognizes an abnormal portion, and prevent the doctor from missing the abnormal portion.

Thus, the information processing apparatus 2000 according to the present example embodiment performs an operation as follows. First, the information processing apparatus 2000 acquires the video data 12, and image-analyzes the video frame 14 constituting the video data 12. Specifically, the information processing apparatus 2000 detects an abnormal region 30 in the video frame 14. The abnormal region 30 is a region inferred to represent an abnormal portion inside a body of a subject. For example, the abnormal region 30 in FIG. 1 is a region (region representing a lesion) including a tumor. In other words, the information processing apparatus 2000 detects, in the video frame 14, one or more image regions having a high probability (for example, equal to or more than a predetermined threshold value) of representing an abnormal portion inside a body, and handles each detected image region as the abnormal region 30.

The information processing apparatus 2000 outputs output information, based on detection of the abnormal region 30. For example, the output information is a mark (such as a frame) representing a position of the abnormal region 30 in the video frame 14. For example, when the information processing apparatus 2000 outputs the video data 12 to a display apparatus in such a way that a user can view the video data 12, the information processing apparatus 2000 superimposes a mark representing a position of the abnormal region 30 on the video frame 14 in which the abnormal region 30 is detected, and outputs the video data 12. In this way, a user who views the video data 12 can easily recognize an abnormal portion inside a body.

In addition, for example, the output information may be data representing a predetermined sound such as a beep. By outputting such a predetermined sound, a user who hears the sound can easily recognize detection of an abnormal portion inside the body.

Herein, when outputting based on detection of the abnormal region 30 is performed in such a manner, a method of "outputting output information when the abnormal region 30 is detected, and not outputting output information when the abnormal region 30 is not detected" is conceivable as a naive technique. For example, when the above-mentioned example in which a mark representing a position of the abnormal region 30 is superimposed on the video frame 14 is considered, a method of superimposing a mark representing a position of the abnormal region 30 on the video frame 14 when the abnormal region 30 is detected, and not superimposing such a mark on the video frame 14 when the abnormal region 30 is not detected is used.

However, this method has a high probability that output information is difficult to handle (view or hear) for a user. The reason is that, when the plurality of video frames 14 are acquired by capturing an abnormal portion inside a body, the abnormal region 30 is not necessarily detected in all of the video frames 14, and the video frame 14 in which the abnormal region 30 is not detected may also be present (the reason will be described later). If the above-mentioned naive technique is applied under such a circumstance, output information is sometimes output and at other times not output even though the video data 12 are acquired by capturing almost the same range inside a body. For example, with the above-described mark, even when the video data 12 acquired by capturing almost the same range inside a body are viewed by a user, the mark is sometimes displayed and at other times not displayed, and thus the mark appears to flash at a short irregular time interval to the user's eyes.

Now, the information processing apparatus 2000 performs an operation as follows. First, the information processing apparatus 2000 computes a score (hereinafter, a detection score) related to a proportion of the number of the video frames 14 in which the abnormal region 30 is detected in a state where outputting of output information is not being performed, and starts outputting of the output information when the detection score becomes equal to or more than a first threshold value. In other words, outputting of the output information is not performed while the detection score is less than the first threshold value. For example, the detection score is computed as a proportion of the number of the video frames 14 in which the abnormal region 30 is detected among a predetermined number of the video frames 14 in which detection of the abnormal region 30 is tried (i.e., the number of the video frames 14 in which the abnormal region 30 is detected/the predetermined number described above).

In this way, outputting of the output information is not performed until a proportion of the number of the video frames 14 in which the abnormal region 30 is detected increases to a certain degree, and thus outputting of the output information is not performed when the abnormal region 30 is detected for only a short time (for example, in only one frame) such as when, for example, noise is mistakenly detected as the abnormal region 30. Thus, the output information can be prevented from being difficult to handle for a user.

Further, the information processing apparatus 2000 also computes a detection score in a state where outputting of output information is being performed, and ends outputting of the output information when the detection score becomes equal to or less than a threshold value. Herein, in a case where the threshold value is set to the same value as the first threshold value (i.e., in a case where outputting of the output information ends when the detection score becomes equal to or less than the first threshold value), for example, when the detection score increases and decreases at a value close to the first threshold value, there is a possibility that the output information is output and is not output repeatedly at a short irregular time interval. Thus, as mentioned above, the output information is difficult to handle for a user.

In this regard, once outputting of the output information starts for the abnormal region 30, it is conceivable that a probability that the abnormal region 30 is mistakenly detected due to noise and the like is low. Thus, in the information processing apparatus 2000, a second threshold value is set to a value smaller than the first threshold value. In this way, once a detection score becomes equal to or more than the first threshold value and outputting of output information starts, even when the detection score becomes equal to or less than the first threshold value after that, outputting of the output information continues while the detection score is equal to or more than the second threshold value. In other words, after a proportion of the number of the video frames 14 in which the abnormal region 30 is detected increases to a certain degree and outputting of output information starts, outputting of the output information continues even when the proportion slightly decreases. Thus, the output information is easy to handle for a user.

Hereinafter, the present example embodiment will be described in more detail.

<Functional Configuration>

Figure 2:
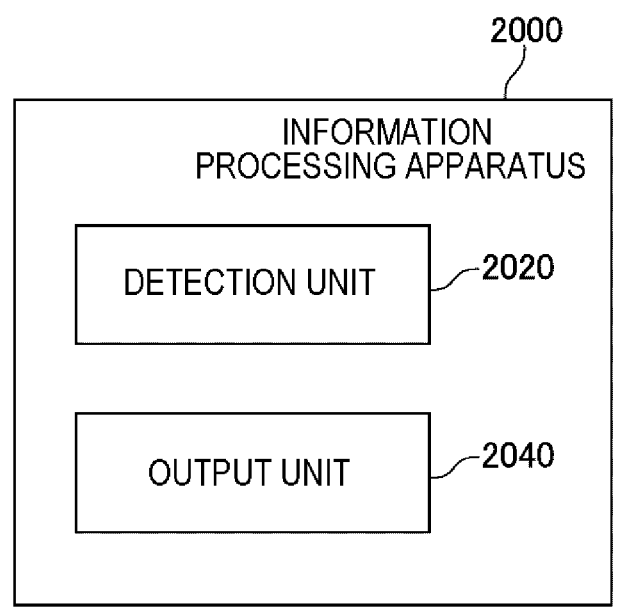
FIG. 2 is a block diagram illustrating a functional configuration of the information processing apparatus.

FIG. 2 is a block diagram illustrating a functional configuration of the information processing apparatus 2000. The information processing apparatus 2000 includes a detection unit 2020 and an output unit 2040. The detection unit 2020 detects the abnormal region 30 in each of the plurality of video frames 14 constituting the video data 12. The output unit 2040 outputs output information related to the detected abnormal region 30. Herein, in a state where outputting of output information is not being performed, the output unit 2040 starts outputting of the output information when a detection score based on a proportion of the number of the video frames 14 in which the abnormal region 30 is detected becomes equal to or more than the first threshold value. On the other hand, in a state where outputting of output information is being performed, the output unit 2040 ends outputting of the output information when the detection score described above becomes equal to or less than the second threshold value.

<Example of Hardware Configuration of Information Processing Apparatus 2000>

Each functional component unit of the information processing apparatus 2000 may be achieved by hardware (for example, a hard-wired electronic circuit and the like) that achieves each functional component unit, and may be achieved by a combination of hardware and software (for example, a combination of an electronic circuit and a program that controls the electronic circuit and the like). Hereinafter, a case where each functional component unit of the information processing apparatus 2000 is achieved by the combination of hardware and software will be further described.

Figure 3:
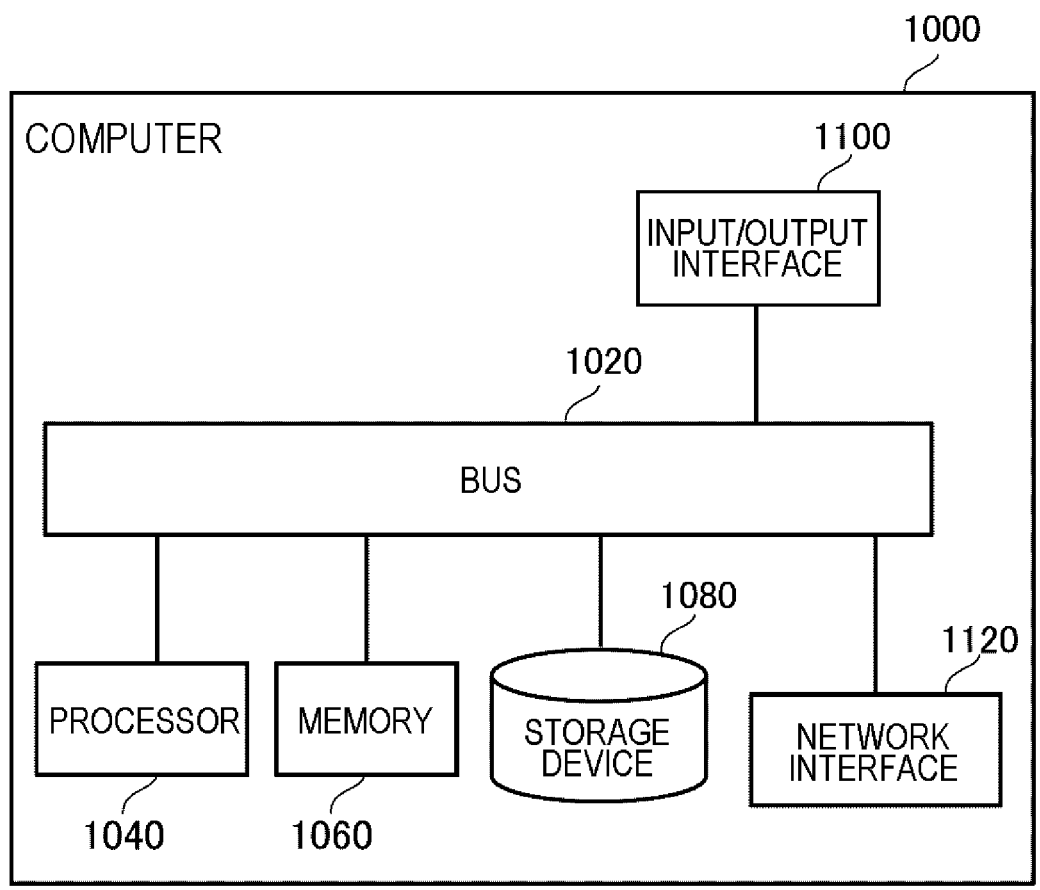
FIG. 3 is a diagram illustrating a computer for achieving the information processing apparatus.

FIG. 3 is a diagram illustrating a computer 1000 for achieving the information processing apparatus 2000. The computer 1000 is any computer. For example, the computer 1000 is a desktop computer such as a personal computer (PC) and a server machine. In addition, for example, the computer 1000 is a portable computer such as a smartphone and a table terminal. The computer 1000 may be a dedicated computer designed for achieving the information processing apparatus 2000, and may be a general-purpose computer.

The computer 1000 includes a bus 1020, a processor 1040, a memory 1060, a storage device 1080, an input/output interface 1100, and a network interface 1120. The bus 1020 is a data transmission path for allowing the processor 1040, the memory 1060, the storage device 1080, the input/output interface 1100, and the network interface 1120 to transmit and receive data from and to one another. However, a method of connecting the processor 1040 and the like to each other is not limited to a bus connection.

The processor 1040 is various types of processors such as a central processing unit (CPU), a graphic processing unit (GPU), and a field-programmable gate array (FPGA). The memory 1060 is a main memory achieved by using a random access memory (RAM) and the like. The storage device 1080 is an auxiliary storage achieved by using a hard disk, a solid state drive (SSD), a memory card, a read only memory (ROM), or the like.

The input/output interface 1100 is an interface for connecting the computer 1000 and an input/output device. For example, the camera 10 and a display apparatus 20 are connected to the input/output interface 1100.

The network interface 1120 is an interface for connecting the computer 1000 to a communication network. The communication network is, for example, a local area network (LAN) and a wide area network (WAN). A method of the network interface 1120 connecting to the communication network may be a wireless connection or a wired connection.

The storage device 1080 stores a program module that achieves each functional component unit of the information processing apparatus 2000. The processor 1040 achieves a function associated with each program module by reading each of the program modules to the memory 1060 and executing the program module.

<Specific Example of Usage Environment of Information Processing Apparatus 2000>

Figure 4:
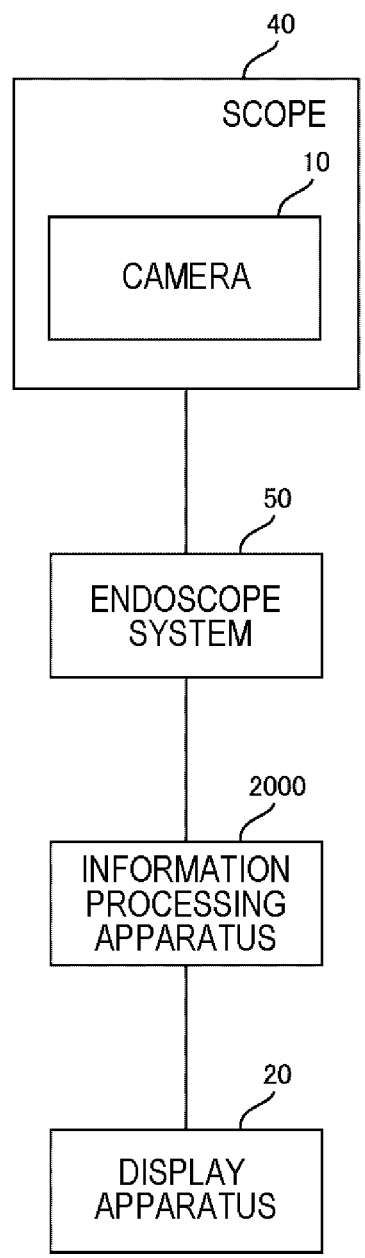
FIG. 4 is a diagram illustrating a specific example of a usage environment of the information processing apparatus.

FIG. 4 is a diagram illustrating a specific example of a usage environment of the information processing apparatus 2000. For example, the information processing apparatus 2000 is used together with a scope 40 and an endoscope system 50. The scope 40 is connected to the endoscope system 50. Further, the camera 10 is provided in the scope 40. In this case, the video data 12 are constituted by the plurality of video frames 14 generated by the camera 10 provided in the scope 40. The endoscope system 50 outputs the video data 12 to the information processing apparatus 2000. For example, the video data 12 are output from a video output interface (for example, a high-definition multimedia interface (HDMI) (registered trademark) interface) provided in the endoscope system 50 to a video input interface included in the information processing apparatus 2000. Then, the information processing apparatus 2000 processes the video data 12 acquired from the endoscope system 50, and performs outputting of output information.

Herein, as described later, the output information may be display provided by using the display apparatus 20, or output in another way. In the former case, the information processing apparatus 2000 controls the display apparatus 20, and causes the display apparatus 20 to display the video data 12 together with the output information. On the other hand, in the latter case, a process of causing the display apparatus 20 to display the video data 12 may be performed by the information processing apparatus 2000, and may by performed by another apparatus (for example, the endoscope system 50). When the process of causing the display apparatus 20 to display the video data 12 is performed by the endoscope system 50, the display apparatus 20 does not need to be connected to the information processing apparatus 2000.

It should be noted that the configuration illustrated in FIG. 4 is merely an exemplification, and a usage environment of the information processing apparatus 2000 is not limited to the configuration illustrated in FIG. 4. For example, the information processing apparatus 2000 may be provided inside the camera 10, the endoscope system 50, or the display apparatus 20. In addition, for example, the video data 12 may be output from the camera 10 to the information processing apparatus 2000. In this case, the information processing apparatus 2000 may not be connected to the endoscope system 50.

<Flow of Processing>

Figure 5:
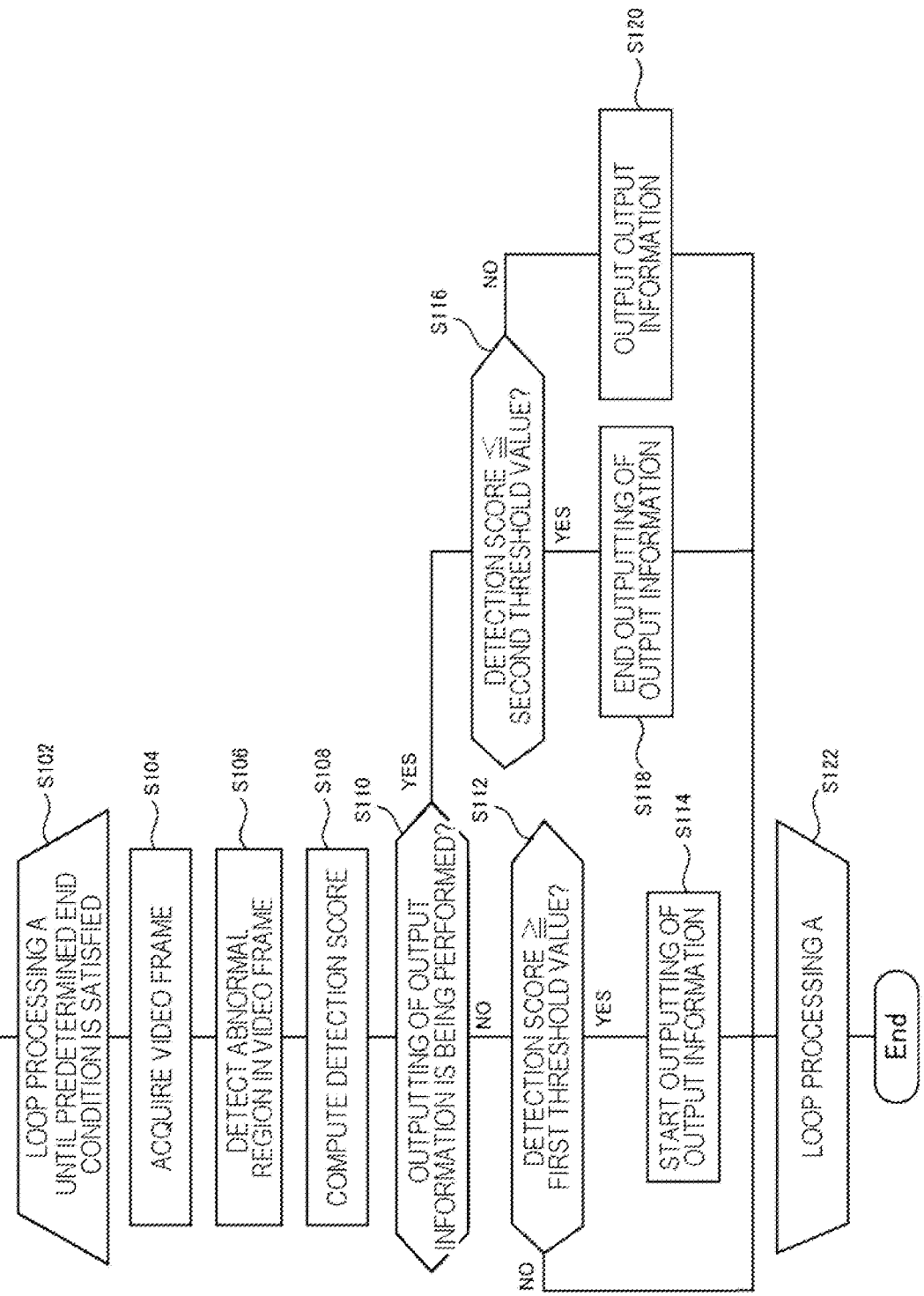
FIG. 5 is a flowchart illustrating a flow of processing performed by the information processing apparatus according to the example embodiment 1.
Figure 6A:
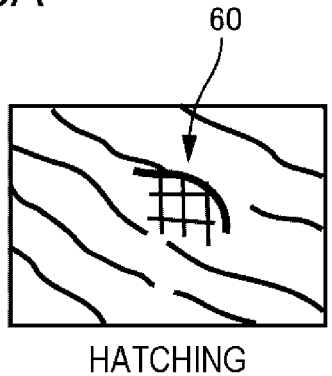
FIGS. 6A-6F are diagrams illustrating a variation of a mark representing a position of an abnormal region.
Figure 6B:
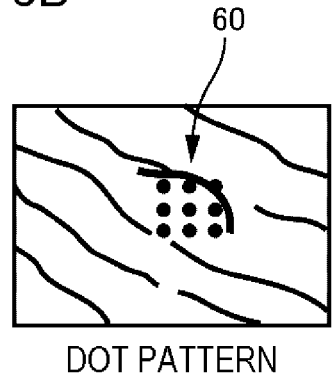
Figure 6C:
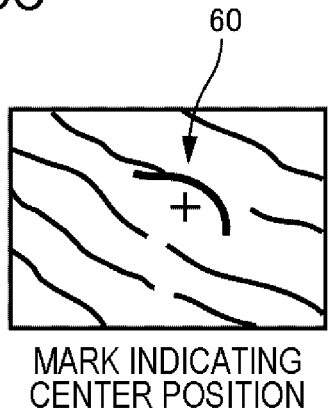
Figure 6D:
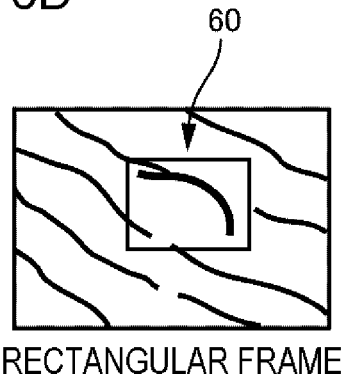
Figure 6E:
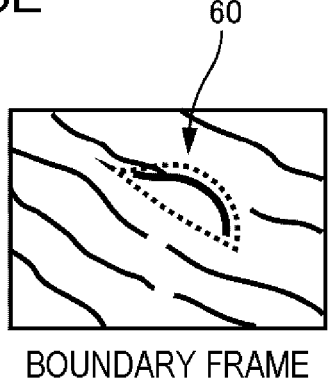
Figure 6F:
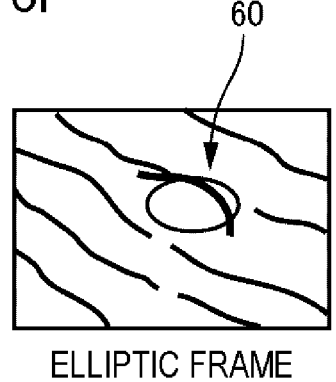

FIG. 5 is a flowchart illustrating a flow of processing performed by the information processing apparatus 2000 according to the example embodiment 1. S102 to S122 are loop processing A repeatedly performed until a predetermined end condition is satisfied. Any end condition is set in advance as the predetermined end condition. For example, the predetermined end condition is reception of a predetermined input operation (such as a press on an end button) from a user.

The information processing apparatus 2000 determines whether the predetermined end condition is satisfied (S102). When the predetermined end condition is satisfied, the processing in FIG. 5 ends. On the other hand, when the predetermined end condition is not satisfied, the processing in FIG. 5 proceeds to S104.

The output unit 2040 acquires a video frame to be processed (S104). The video frame 14 to be processed by the detection unit 2020 is, for example, a video frame having the earliest generation time among the video frames 14 that are not processed yet. The detection unit 2020 performs detection of the abnormal region 30 on the video frame to be processed (S106). The output unit 2040 computes a detection score (S108). The output unit 2040 determines whether outputting of output information is being performed (S110).

In a case where outputting of the output information is not being performed (S110: NO), the output unit 2040 determines whether the detection score is equal to or more than a first threshold value (S112). When the detection score is equal to or more than the first threshold value (S112: YES), the output unit 2040 starts outputting of the output information (S114).

In a case where outputting of the output information is being performed (S110: YES), the output unit 2040 determines whether the detection score is equal to or less than a second threshold value (S116). When the detection score is equal to or less than the second threshold value (S116: YES), the output unit 2040 ends outputting of the output information (S118). When the detection score is more than the second threshold value (S116: NO), the output unit 2040 outputs the output information (S120).

S122 is the end of the loop processing A, and thus the processing in FIG. 5 returns to S102.

<Acquisition of Video Frame 14: S104>

The detection unit 2020 acquires the video frame 14 to be processed (S104). Any method of acquiring the video frame 14 by the acquisition unit 2020 can be used. For example, the detection unit 2020 acquires the video frame 14 by accessing a storage apparatus that stores the video frame 14. The storage apparatus that stores the video frame 14 may be provided inside the camera 10, and may be provided outside the camera 10. Further, for example, the detection unit 2020 may acquire the video frame 14 by receiving the video frame 14 transmitted from the camera 10. Furthermore, the detection unit 2020 may acquire the video frame 14 from another apparatus (for example, the endoscope system 50 mentioned above) connected to the camera 10.

It should be noted that, when the detection unit 2020 acquires the video frame 14, the detection unit 2020 may acquire the video frame 14 one by one, or may acquire the plurality of video frames 14 all together (for example, collectively acquire all of the video frames 14 constituting the video data 12). In the former case, for example, each time a new video frame 14 is generated by the camera 10, the detection unit 2020 acquires the video frame 14. In the latter case, for example, the detection unit 2020 acquires, at a predetermined time interval, the plurality of video frames 14 that are not acquired yet.

<Detection of Abnormal Region 30: S106>

The detection unit 2020 detects the abnormal region 30 in each of the video frames 14 constituting the video data 12 (S106). Specifically, the detection unit 2020 detects, in the video frame 14, an image region having likelihood of representing an abnormal portion inside a body being equal to or more than a threshold value, and sets the image region as the abnormal region 30. Herein, an existing technique can be used as a technique for detecting an image region representing an abnormal portion inside a body by analyzing an image in which the inside of the body is captured.

For example, a technique such as feature value matching and template matching can be used for detection of the abnormal region 30. For example, when a tumor is detected by feature value matching, one or more values (feature values) representing a feature of an appearance (such as a color, a pattern, or a shape) of the tumor are defined in advance. The detection unit 2020 detects, in the video frame 14, an image region having a degree of similarity to the predetermined feature value of the tumor being equal to or more than a threshold value among image regions of the video frame 14. Then, the detection unit 2020 handles the detected image region as an image region representing the abnormal region 30. A similar method can also be adopted in a case of detecting a wound and a foreign body.

In addition, for example, a detector that detects the abnormal region 30 in the video frame 14 may be generated by machine learning, and detection of the abnormal region 30 may be performed by using the detector. Various models such as a neural network and a support vector machine can be adopted as a model of the detector. It should be noted that an existing technique can be used as a technique for generating, by machine learning, a detector that detects a region having a specific feature in an image.

It should be noted that it is assumed that a foreign body having entered a body is identified in a case where the foreign body is desired to be detected. In this case, it is suitable to be able to specify a feature value of the foreign body to the information processing apparatus 2000. For example, a picture of a foreign body having entered a body is input to the information processing apparatus 2000. The information processing apparatus 2000 computes a feature value of the foreign body to be detected by image-analyzing the picture. Then, the detection unit 2020 detects the foreign body having the computed feature value in the video frame 14.

<Computation of Detection Score: S108>

The output unit 2040 computes a detection score (S108). As mentioned above, the detection score is computed based on a proportion of the number of the video frames 14 in which the abnormal region 30 is detected. For example, the output unit 2040 computes a proportion of the number of the video frames 14 in which the abnormal region 30 is detected, and uses the proportion itself as a detection score.

Herein, various methods can be adopted as a method of computing a proportion of the number of the video frames 14 in which the abnormal region 30 is detected. For example, when the output unit 2040 performs the process of detecting the abnormal region 30 on a certain video frame 14, the output unit 2040 sets, as a proportion of the number of the video frames 14 in which the abnormal region 30 is detected, a value of a proportion (the number of the video frames 14 in which the abnormal region 30 is detected/a predetermined number) of the number of the video frames 14 in which the abnormal region 30 is detected among a past predetermined number of the video frames 14 including the certain video frame 14.

For example, it is assumed that the output unit 2040 detects the abnormal region 30 in a video frame X. Further, it is assumed that the abnormal region 30 is detected in five video frames 14 among past 10 video frames 14 including the video frame X. In this case, the output unit 2040 computes ½ as a detection score.

In addition, for example, the output unit 2040 may set, as a detection score, the number itself of the video frames 14 in which the abnormal region 30 is detected. For example, it is assumed that the output unit 2040 detects an abnormal region 30 in a video frame X. Further, it is assumed that the abnormal region 30 is detected in five video frames 14 among past 10 video frames 14 including the video frame X. In this case, the output unit 2040 sets 5 as a detection score.

<<Identification of Abnormal Region 30>>

Herein, a detection score is computed for each abnormal region 30 representing the same abnormal portion. For example, it is assumed that the abnormal region 30 representing an abnormal portion A and the abnormal region 30 representing an abnormal portion B are detected in a certain video frame X. In this case, the output unit 2040 computes each of a detection score based on a proportion of the number of the video frames 14 in which the abnormal region 30 representing the abnormal portion A is detected, and a detection score based on the number of the video frames 14 in which the abnormal region 30 representing the abnormal portion B is detected. For example, it is assumed that, among past 10 video frames 14 including the video frame X, the video frame 14 in which the abnormal region 30 representing the abnormal portion A is detected is five, and the video frame 14 in which the abnormal region 30 representing the abnormal portion B is detected is three. In this case, the output unit 2040 computes ½ as a detection score of the abnormal region 30 representing the abnormal portion A, and computes 3/10 as a detection score of the abnormal region 30 representing the abnormal portion B.

In order to compute a detection score for abnormal regions 30 representing the same abnormal portion in such a manner, the detection unit 2020 divides the plurality of abnormal regions 30 detected in the video frames 14 different from each other into groups in each of which the abnormal regions 30 represent the same abnormal portion. In other words, identification of the abnormal region 30 is performed. Then, the output unit 2040 computes a detection score mentioned above for each group of the abnormal regions 30 representing the same abnormal portion.

Herein, an existing technique for performing identification on an object detected in each video frame of video data can be used for identification of the abnormal region 30. For example, identification of the abnormal region 30 can be performed based on a degree of similarity of a feature value of the abnormal region 30.

<Weighting Based on Likelihood>

A detection score computed by the output unit 2040 may not be the number of the video frames 14 in which the abnormal region 30 is detected and a proportion itself. As mentioned above, the detection unit 2020 computes, for each abnormal region 30, likelihood that the abnormal region 30 represents an abnormal portion. Thus, for example, the output unit 2040 computes, for a past predetermined number of the video frames 14, statistics (such as an integrated value and an average value) of likelihood that each abnormal region 30 (abnormal region 30 representing the same abnormal portion) belonging to the same group represents the abnormal portion, and computes the statistics as a detection score of the abnormal region 30.

For example, it is assumed that the predetermined number described above is 10, and the detection unit 2020 detects the abnormal region 30 representing the same abnormal portion A in three video frames X, Y, and Z among past 10 video frames 14. Then, it is assumed that likelihood of representing the abnormal portion is 0.9, 0.7, and 0.4 in the abnormal regions 30 detected in the video frames X, Y, and Z, respectively. In this case, the output unit 2040 computes, as a detection score of the abnormal region 30 representing the abnormal portion A, 2.0 being an integrated value of the likelihood.

It should be noted that the output unit 2040 may set, as a detection score, a value acquired by dividing the integrated value of the likelihood by the predetermined number described above instead of the above-mentioned integrated value of the likelihood.

<Determination of Whether Outputting is Being Performed: S110>

The output unit 2040 determines whether outputting of output information is being performed (S110). For example, the determination is achieved by storing an output flag representing a state of output in a storage apparatus, and referring to the output flag. For example, the output flag represents a non-output state when a value is 0, and represents an output state when a value is 1. An initial value of the output flag is set to 0.

The output unit 2040 determines that outputting of the output information is being performed when the value of the output flag is 1. On the other hand, the output unit 2040 determines that outputting of the output information is not being performed when the value of the output flag is 0. Further, when the output unit 2040 starts outputting of the output information (S114), the output unit 2040 changes the value of the output flag to 1. On the other hand, when the output unit 2040 ends outputting of the output information (S118), the output unit 2040 changes the value of the output flag to 0.

<Outputting of Output Information: S114 and S120>

In a state where outputting of the output information is not being performed (S110: NO), the output unit 2040 starts outputting of the output information (S114) when the detection score becomes equal to or more than the first threshold value (S112: YES). Further, in a state where outputting of the output information is being performed (S110: YES), the output unit 2040 outputs the output information (S120) when the detection score is more than the second threshold value (S116: NO). For example, the output information is display and a sound. Hereinafter, a case of each of display and a sound is illustrated.

<<Output of Display>>

Various types of display can be adopted for display based on detection of the abnormal region 30. For example, display based on detection of the abnormal region 30 is a mark representing a position of the abnormal region 30 detected in the video frame 14. In other words, the output unit 2040 superimposes, on the video frame 14 to be processed, a mark representing a position of the abnormal region 30 detected in the video frame 14. FIGS. 6A-6F are diagrams illustrating a variation of a mark 60 representing a position of the abnormal region 30.

For example, the output unit 2040 outputs the video data 12 (the plurality of video frames 14) to the display apparatus 20. At this time, for a case where outputting of output information is not performed, the output unit 2040 outputs the video frame 14 as it is. On the other hand, for a case where outputting of output information is performed, the output unit 2040 outputs the video frame 14 on which the mark 60 is superimposed.

Figure 7:
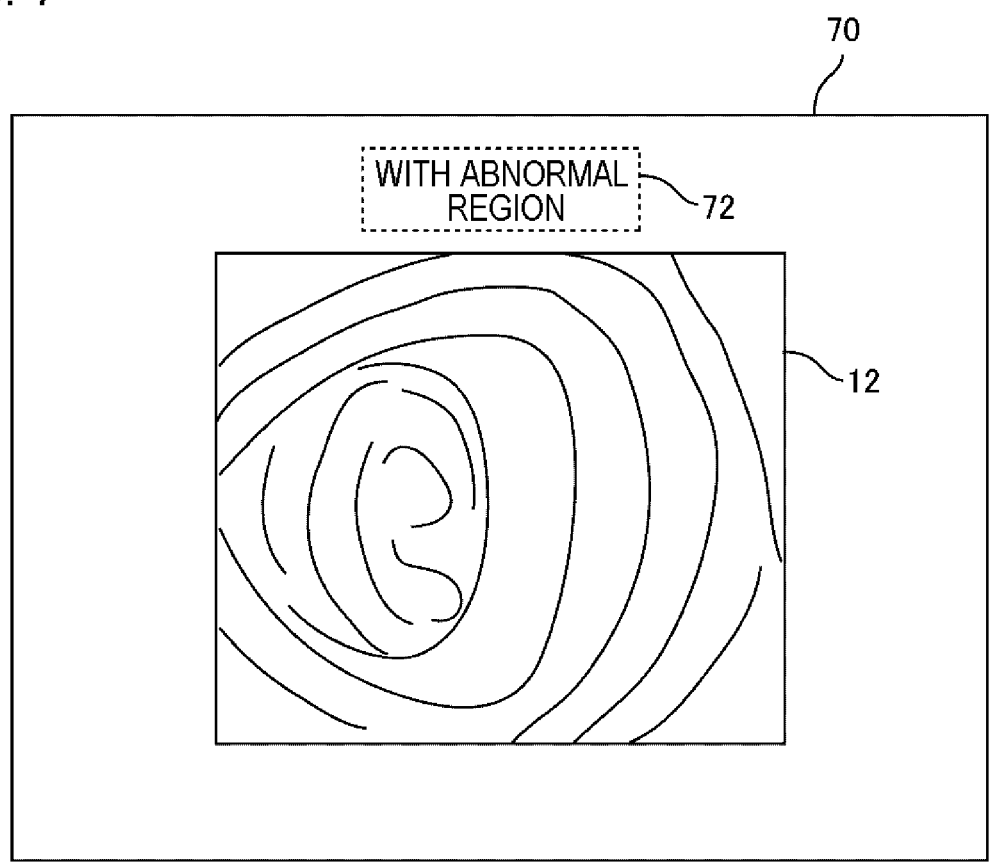
FIG. 7 is a diagram illustrating a message indicating that an abnormal region is included in a video frame.

In addition, for example, display based on detection of the abnormal region 30 is a message representing that the abnormal region 30 is included in the video frame 14. FIG. 7 is a diagram illustrating a message representing that the abnormal region 30 is included in the video frame 14. In FIG. 7, the output unit 2040 causes the display apparatus 20 to display a window 70 including the video data 12. In a state where output information is output, the output unit 2040 causes a message 72 to be displayed on the video data 12.

Herein, as mentioned above, in a case where, without considering a detection score, the message 72 is output in an aspect in which the message 72 is output when the abnormal region 30 is detected in the video frame 14 and the message 72 is not output (is deleted) when the abnormal region 30 is not detected in the video frame 14, display and non-display of the message 72 may be repeated at a short irregular time interval. As a result, it appears to a user that the message 72 irregularly flashes, and the message 72 is difficult to see.

In this regard, according to the information processing apparatus 2000, repetition of display and non-display of the message 72 at a short irregular time interval does not occur by performing control in consideration of a detection score, and thus it is easy for a user to see the message 72.

In addition, for example, display based on detection of the abnormal region 30 is display that emphasizes the video frame 14 including the abnormal region 30. For example, as an example of emphasized display, there are ways of thickening a frame of the video frame 14 and changing a color of a frame of the video frame 14. Even such emphasized display makes it difficult for a user to see when a detection score is not considered. For example, a frame of the video frame 14 changes at a short irregular time interval. In this regard, according to the information processing apparatus 2000, such a change in a frame of the video frame 14 at a short irregular time interval does not occur, and emphasized display can be achieved in an mode that makes it easy for a user to see.

Herein, the output unit 2040 may display a plurality of types of various types of the display mentioned above. For example, in FIG. 7, the mark 60 representing a position of the abnormal region 30 may be displayed in addition to the message 72.

An output destination of output information is not limited to the display apparatus. For example, the output unit 2040 may store, in the storage apparatus, the video data 12 on which output information is superimposed.

<<Output of Sound>>

The output unit 2040 may output a sound instead of display based on detection of the abnormal region 30 or together with the display. For example, in a state where outputting is not being performed (S110: NO), the output unit 2040 starts outputting of sound data representing a predetermined sound (for example, a beep) (S114) when the detection score becomes equal to or more than the first threshold value (S112: YES). Then, in a state where outputting is being performed (S110: YES), the output unit 2040 ends outputting of the predetermined sound (S118) when the detection score becomes equal to or less than the second threshold value (S116: YES).

The sound data are output to, for example, a speaker connected to the information processing apparatus 2000. In this way, a predetermined sound represented by the sound data is output from the speaker. Further, the sound data are stored in advance in a storage apparatus that can be accessed from the output unit 2040.

It is assumed that a sound is output in response to detection of the abnormal region 30 without considering a detection score. In this case, due to a similar reason for a risk that output and non-output of display may be repeated at a short irregular time interval, there is a risk that output and non-output of a sound may be repeated at a short irregular time interval, and the sound is difficult for a user to hear.

Example Embodiment 2

Figure 8:
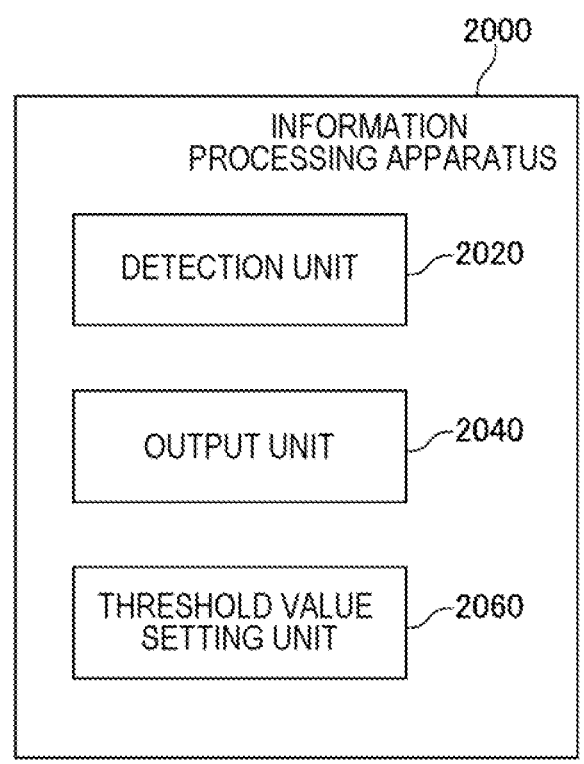
FIG. 8 is a block diagram illustrating a functional configuration of an information processing apparatus according to an example embodiment 2.

FIG. 8 is a block diagram illustrating a functional configuration of an information processing apparatus 2000 according to an example embodiment 2. The information processing apparatus 2000 according to the example embodiment 2 includes a function similar to that of the information processing apparatus 2000 according to the example embodiment 1 except for a matter described below.

The information processing apparatus 2000 according to the example embodiment 2 includes a threshold value setting unit 2060. The threshold value setting unit 2060 sets a first threshold value for each group of abnormal regions 30 representing the same abnormal portion. Thus, an output unit 2040 compares a detection score computed for each group of the abnormal regions 30 representing the same abnormal portion with the first threshold value set for the group.

For example, an initial value of the first threshold value set for each group is all the same value. Then, the threshold value setting unit 2060 changes the first threshold value of a group (i.e., a group in which outputting of output information is already performed) in which outputting of output information ends to a value smaller than the initial value. Herein, it can be said that a probability that the abnormal region 30 belonging to a group in which output information is already output is a region mistakenly detected due to noise and the like is low. Thus, by changing the first threshold value of such an abnormal region 30 to a smaller value, when the abnormal region 30 representing a certain abnormal portion is no longer detected in video data 12 (for example, the abnormal region 30 gets out of the frame), and then the abnormal region 30 representing the certain abnormal portion is detected again (for example, the abnormal region 30 gets in the frame again), a probability that output information regarding the abnormal region 30 is to be output can be increased.

<Hardware Configuration>

A hardware configuration of a computer that achieves the information processing apparatus 2000 according to the example embodiment 2 is represented, for example, in FIG. 3, similarly to the example embodiment 1. However, a program module that achieves a function of the information processing apparatus 2000 according to the present example embodiment is further stored in a storage device 1080 of a computer 1000 that achieves the information processing apparatus 2000 according to the present example embodiment.

While the example embodiments of the present invention have been described with reference to the drawings, the example embodiments are only exemplification of the present invention, and combination of each of the above-described example embodiments or various configurations other than the above-described example embodiments can also be employed.

A part or the whole of the above-described embodiments may also be described as in supplementary notes below, which is not limited thereto.

1. An information processing apparatus, including:
   a detection unit that detects an abnormal region, which is an image region inferred to represent an abnormal portion inside a body, in each of a plurality of video frames constituting a video in which the inside of the body is captured; and
   an output unit that outputs output information related to the detected abnormal region, in which
   the output unit
      starts outputting of the output information when a score based on a proportion of the number of video frames in which the abnormal region is detected becomes equal to or more than a first threshold value in a state where outputting of the output information is not being performed, and
      ends outputting of the output information when the score becomes equal to or less than a second threshold value in a state where outputting of the output information is being performed, and
   the second threshold value is smaller than the first threshold value.

2. The information processing apparatus according to supplementary note 1, in which
   the output unit computes the score for each group of the abnormal region representing the same abnormal portion.

3. The information processing apparatus according to supplementary note 2, in which
   the output unit computes, for a group of the abnormal region representing the same abnormal portion, statistics of likelihood that each abnormal region included in the group represents an abnormal portion inside the body, and sets a value based on the statistics as the score for the group.

4. The information processing apparatus according to any one of supplementary notes 1 to 3, further including
   a threshold value setting unit that sets the first threshold value for each group of the abnormal region representing the same abnormal portion, in which
   the output unit compares a score computed for each group of the abnormal region representing the same abnormal portion with the first threshold value set for the group, and
   the threshold value setting unit changes, to a smaller value, the first threshold value of a group in which outputting of the output information ends.

5. A control method being executed by a computer, including:
   a detection step of detecting an abnormal region, which is an image region inferred to represent an abnormal portion inside a body, in each of a plurality of video frames constituting a video in which the inside of the body is captured; and
   an output step of outputting output information related to the detected abnormal region, in which
   in the output step,
      outputting of the output information is started when a score based on a proportion of the number of video frames in which the abnormal region is detected becomes equal to or more than a first threshold value in a state where outputting of the output information is not being performed, and
      outputting of the output information is ended when the score becomes equal to or less than a second threshold value in a state where outputting of the output information is being performed, and
   the second threshold value is smaller than the first threshold value.

6. The control method according to supplementary note 5, in which
   in the output step, the score is computed for each group of the abnormal region representing the same abnormal portion.

7. The control method according to supplementary note 6, in which
   in the output step, for a group of the abnormal region representing the same abnormal portion, statistics of likelihood that each abnormal region included in the group represents an abnormal portion inside the body is computed, and a value based on the statistics is set as the score for the group.

8. The control method according to any one of supplementary notes 5 to 7, further including
a threshold value setting step of setting the first threshold value for each group of the abnormal region representing the same abnormal portion, in which
in the output step, a score computed for each group of the abnormal region representing the same abnormal portion is compared with the first threshold value set for the group, and
in the threshold value setting step, the first threshold value of a group in which outputting of the output information ends is changed to a smaller value.

9. A program causing a computer to execute each step of the control method according to any one of supplementary notes 5 to 8.

The invention claimed is:

1. An information processing apparatus, comprising:
at least one memory configured to store instructions; and
at least one processor configured to execute the instructions to perform operations comprising:
detecting an abnormal region, which is an image region inferred to represent an abnormal portion inside a body, in each of a plurality of video frames constituting a video in which the inside of the body is captured;
analyzing the plurality of video frames to determine a proportion of a number of video frames in which the abnormal region is detected;
starting outputting of output information related to the detected abnormal region when a score based on the proportion becomes equal to or more than a first threshold value in a state where outputting of the output information is not being performed; and
ending outputting of the output information when the score becomes equal to or less than a second threshold value in a state where outputting of the output information is being performed,
wherein the second threshold value is smaller than the first threshold value.

2. The information processing apparatus according to claim 1, wherein
the operations further comprise computing the score for each group of the abnormal region representing a same abnormal portion.

3. The information processing apparatus according to claim 2, wherein
the computing comprises computing, for a group of the abnormal region representing a same abnormal portion, statistics of likelihood that each abnormal region included in the group represents the abnormal portion inside the body, and setting a value based on the statistics as the score for the group.

4. The information processing apparatus according to claim 1, wherein
the operations further comprise setting the first threshold value for each group of the abnormal region representing a same abnormal portion,
the outputting the output information comprises comparing the score computed for each group of the abnormal region representing a same abnormal portion with the first threshold value set for the group, and
the setting the first threshold value comprises changing, to a smaller value, the first threshold value of the group in which outputting of the output information ends.

5. A control method being executed by a computer, comprising:
detecting an abnormal region, which is an image region inferred to represent an abnormal portion inside a body, in each of a plurality of video frames constituting a video in which the inside of the body is captured;
analyzing the plurality of video frames to determine a proportion of a number of video frames in which the abnormal region is detected;
starting outputting of output information related to the detected abnormal region when a score based on the proportion becomes equal to or more than a first threshold value in a state where outputting of the output information is not being performed; and
ending outputting of the output information when the score becomes equal to or less than a second threshold value in a state where outputting of the output information is being performed,
wherein the second threshold value is smaller than the first threshold value.

6. The control method according to claim 5, wherein
the score is computed for each group of the abnormal region representing a same abnormal portion.

7. The control method according to claim 6, wherein
for a group of the abnormal region representing a same abnormal portion, statistics of likelihood that each abnormal region included in the group represents the abnormal portion inside the body is computed, and a value based on the statistics is set as the score for the group.

8. The control method according to claim 5, further comprising
setting the first threshold value for each group of the abnormal region representing a same abnormal portion, wherein
the score computed for each group of the abnormal region representing a same abnormal portion is compared with the first threshold value set for the group, and
the first threshold value of the group in which outputting of the output information ends is changed to a smaller value.

9. A non-transitory storage medium storing a program causing a computer to execute a control method, the control method comprising:
detecting an abnormal region, which is an image region inferred to represent an abnormal portion inside a body, in each of a plurality of video frames constituting a video in which the inside of the body is captured;
analyzing the plurality of video frames to determine a proportion of a number of video frames in which the abnormal region is detected;
starting outputting of output information related to the detected abnormal region when a score based on the proportion becomes equal to or more than a first threshold value in a state where outputting of the output information is not being performed;
ending outputting of the output information when the score becomes equal to or less than a second threshold value in a state where outputting of the output information is being performed,
wherein the second threshold value is smaller than the first threshold value.

10. The information processing apparatus according to claim 1, wherein
in a state where outputting of the output information is being performed, even when the detection score becomes equal to or less than the first threshold value, outputting of the output information is continued while the detection score is more than the second threshold value.

11. The information processing apparatus according claim 1, wherein
- detecting the abnormal region comprises using a detector that detects the abnormal region, the detector being generated by machine learning, and
- the operations optimize the output information so that it is easy for users to see the output information.

12. The control method according to claim 5, wherein
- in a state where outputting of the output information is being performed, even when the detection score becomes equal to or less than the first threshold value, outputting of the output information is continued while the detection score is more than the second threshold value.

13. The non-transitory storage medium according to claim 9, wherein
- in a state where outputting of the output information is being performed, even when the detection score becomes equal to or less than the first threshold value, outputting of the output information is continued while the detection score is more than the second threshold value.

* * * * *